United States Patent [19]
Rongione

[11] Patent Number: 5,852,208
[45] Date of Patent: Dec. 22, 1998

[54] METHOD OF PRODUCING COMPOUNDS CONTAINING ACYLOXYALKOXY GROUPS FROM ALCOHOLS

[75] Inventor: Joseph C. Rongione, Webster, Tex.

[73] Assignee: Dixie Chemical Company, Inc., Pasadena, Tex.

[21] Appl. No.: 705,713

[22] Filed: Aug. 30, 1996

[51] Int. Cl.$^6$ .......................... C07C 69/02; C07C 409/00
[52] U.S. Cl. .......................... 560/231; 560/240; 568/559; 568/563; 568/567; 568/591; 568/593; 568/594
[58] Field of Search .................................. 560/231, 240; 568/559, 563, 567, 591, 593, 594

[56] References Cited

U.S. PATENT DOCUMENTS

| | | | |
|---|---|---|---|
| 2,512,950 | 6/1950 | Londergan | 528/242 |
| 2,848,437 | 8/1958 | Langsdorf et al. | 260/67 |
| 2,964,500 | 12/1960 | Jenkins et al. | 260/67 |
| 2,998,409 | 8/1961 | Nogare et al. | 260/67 |
| 3,000,860 | 9/1961 | Brown et al. | 528/243 |
| 3,193,533 | 7/1965 | Manwiller et al. | 528/239 |
| 3,316,219 | 4/1967 | Wagner et al. | 528/237 |
| 3,425,991 | 2/1969 | Mortillaro et al. | 525/398 |
| 3,609,124 | 9/1971 | Ackermann et al. | 260/67 FP |
| 3,687,898 | 8/1972 | Ishii et al. | 525/400 |
| 3,687,989 | 8/1972 | Ishii et al. | 260/67 FP |
| 3,875,117 | 4/1975 | Ackermann et al. | 260/67 R |
| 4,355,032 | 10/1982 | Verheyden et al. | 424/253 |
| 5,171,879 | 12/1992 | Gallegra et al. | 560/266 |
| 5,175,348 | 12/1992 | Gallegra et al. | 560/266 |

FOREIGN PATENT DOCUMENTS 0 187 297 A2  7/1986  European Pat. Off. .

OTHER PUBLICATIONS

Chemical Abstracts No. 113:39955a; Preparation of 1,3–diacetoxy–2–acetoxymethoxypropane as an intermediate for radiosensitizers, Feb. 19, 1990.

Chemical Abstract No. 103:6658n; Synthesis and antiherpetic activity of (S)–,(R)–,and (±)–9–[(2,3–dihydroxy–1–propoxy)methyl]guanine, linear isomers of 2'–nor–2'–deoxyguanosine, J. Med. Chem. 1985, 28(7), 926–933.

Chemical Abstract No. 99: 53485n; Antiviral guanine derivatives, Mar. 16, 1983.

Mamedov et al., "Glycol Ethers. . Their Derivatives", J. Gen. Chem. of the USSR, 34(7), pp 2900–2905.

Matsuzaki et al., "New Plolyacetal. . . Transfer Agent", Bulletin Chem. Soc. Jpn, 67(9). pp 2560–2565.

*Primary Examiner*—Gary Geist
*Assistant Examiner*—Rosalynd Keys
*Attorney, Agent, or Firm*—Liddell, Sapp, Zivley, Hill & LaBoon, L.L.P.

[57] ABSTRACT

A process of producing compounds containing an acyloxyalkoxy group from an alcohol consists of reacting the alcohol with a formaldehyde donor until a compound of the formula:

$$R\text{—}O\text{—}CH_2(OCH_2)_xOR \qquad (V)$$

is generated, wherein x is between about 1 to about 5 and R is an organic moiety. This product is then reacted with a carboxylic acid anhydride. The resulting product has the formula:

$$R\text{—}O\text{—}CH_2O\text{—}COR^1$$

wherein $R^1$ is a $C_1$–$C_6$ alkyl group. The invention further relates to intermediates used in the production of such acyloxyalkoxylated compounds.

24 Claims, No Drawings

METHOD OF PRODUCING COMPOUNDS CONTAINING ACYLOXYALKOXY GROUPS FROM ALCOHOLS

BACKGROUND OF THE INVENTION

A number of compounds used as pharmaceutical intermediates contain the acyloxyalkoxy group,

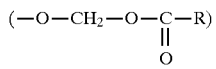

These intermediates include: 1,3-propanediol, 2-[(acetyloxy)methoxy] diacetate represented by the formula:

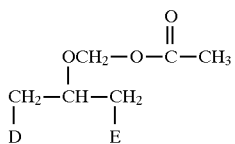

wherein D and E are both

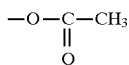

as well as [2-(phenylmethoxy)-1-[(phenylmethoxy)methyl] ethoxy] acetate, represented by the formula (A) above wherein D and E are both, —OCH$_2$—C$_6$H$_5$; 2-[(acetyloxy) methoxy] acetate represented by the formula:

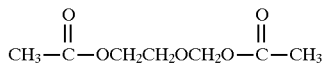

and 1,8 (2H, 5H)-Naphthalenedione, 8a-[[(acetyloxy) methoxy]methyl]-3,4,4a,8a-tetrahydro-6-(phenylthio)-, cis-(+/−)- repesented by the formula:

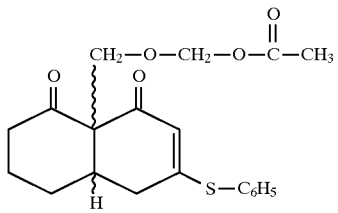

These intermediates are used in the manufacture of a broad range of antitumor, antiviral, antibacterial and agricultural products. Some of the products made from these intermediates are N-alkoxyalkylpyrimidine derivatives, ethylene glycol and glycerol derivatives of guanine—see for instance, U.S. Pat. No. 4,355,032—and functionalized decalin derivatives for Spruce Budworm (Choristoneura fumiferana), (see Can. J. Chem. 1993, 71 (8), 1184). An example is 9-(1,3-dihydroxy-2-propoxymethyl) guanine, represented by the formula (B):

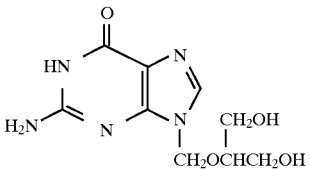

A method of preparing such compounds is set forth in U.S. Pat. No. 4,355,032.

Though there are several methods for the production of compounds containing an acyloxyalkoxy group, the existing methods have certain drawbacks. One common route involves chloromethylation of the alcohol followed by nucleophilic displacement of the chloro group by the salt of a carboxylic acid. This multistep method suffers from the need for dry HCl gas as well as the formation of bis (chloromethyl) ether (BCME), ClCH$_2$OCH$_2$Cl. BCME is a carcinogenic species which must be neutralized as a part of the reaction workup.

Another method uses the chloromethyl ester of a carboxylic acid as the acyloxymethylating agent. The synthesis of the chloromethyl ester has several drawbacks. The raw materials pose disposal problems (zinc salts). Further, the reaction, like the previously mentioned route produces the carcinogen BCME, along with other noxious side products (SO$_2$ and HCl). See U.S. Pat. No. 5,175,348. The liberated HCl can react with other moieties on the desired compound.

A route that bypasses the chloromethylation step involves the transetherification of an acyloxymethoxy group of a simple alcohol, such as methanol. Such is disclosed in European Patent Application 0 187 297. This method requires the synthesis of the transetherification starting material.

The need exists therefore for a method of producing compounds containing an acyloxyalkoxy group for use as pharmaceutical intermediates at milder conditions than those used in currently available routes. Such processes should not generate the carcinogen BCME. Neither should such processes require nor liberate HCl, SO$_2$ or other noxious side products.

SUMMARY OF THE INVENTION

The invention relates to a novel process for producing compounds containing acyloxyalkoxy groups from alcohols. In the first step of the process, a formaldehyde donor is reacted with the alcohol to form a compound of the formula:

$$R\text{—}O\text{—}CH_2(OCH_2)_xOR \quad (V)$$

wherein x is between about 1 to about 5 and further wherein R is the organic moiety of the alcohol. In the second step of the process, the compound of formula (V) is reacted with a carboxylic acid anhydride to generate the compound of the formula:

$$R\text{—}O\text{—}CH_2O\text{—}C\text{—}OR^1 \quad (I)$$

wherein R$^1$ is the organic moiety of the carboxylic acid anhydride. Such compounds have wide applicability in the synthesis of medicaments including the production of 9-(1, 3-dihydroxy-2-propoxymethyl)guanine.

The invention further relates to novel intermediates of (I) wherein R is a substituted alkyl group and R$^1$ is a C$_1$–C$_6$ alkyl group. Such compounds may be employed in the production of such medicaments as 9-(1,3-dihydroxy-2-propoxymethyl)guanine. In particular, these novel intermediates are of the formula (II):

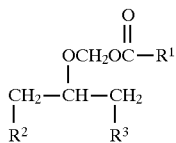

wherein $R^2$ and $R^3$ are halogen.

DETAILED DESCRIPTION OF THE EMBODIMENTS

The process of the invention is directed to the production from alcohols of compounds containing at least one acyloxyalkoxy group. Such compounds have particular utility as intermediates in the preparation of pharmaceuticals.

In the first step of the process, an alcohol is reacted with a formaldehyde donor. The resulting product may be represented by the formula:

$$R\text{—}O\text{—}CH_2(OCH_2)_xOR \quad (V)$$

wherein R is the organic moiety of the alcohol, R—OH, and x is between about 1 to about 5. The R group of the alcohol may be any organic moiety onto which is desired to be introduced an acyloxyalkoxy group. Representative of the R substituent include those containing only carbon and hydrogen, such as allyl, cycloalkyl, and aryl groups as well as those containing carbon and hydrogen atoms as well as oxygen, sulfur, phosphorus, nitrogen or halogen atoms. The R group of the alcohol may thus include phenoxy, benzyloxy, amino, ether, thioether, ester or carbonyl linkages as well as halogen atoms.

In a preferred embodiment, the invention is drawn to a process for the preparation of compounds of the formula:

$$R\text{—}O\text{—}CH_2O\text{—}C\text{—}OR^1 \quad (I)$$

wherein R is a $C_1$–$C_6$ alkyl group, a $C_3$–$C_8$ cycloalkyl group, an aryl group or a benzyl group and further wherein R may be optionally substituted with a phenoxy or benzyloxy group; and $R^1$ is a $C_1$–$C_6$ aliphatic hydrocarbon. In addition, any of the R groups may optionally contain halogen atoms (preferably —Cl or —Br) or a substituent selected from the group consisting of:

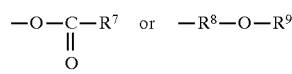

wherein $R^7$ and $R^9$ may independently be a $C_1$ to $C_6$ alkyl group or a haloalkyl group (the halogen being selected from the group consisting of —Cl or —Br) and $R^8$ is a $(CH_2)_y$ group where y is 0 to about 6.

The process of the invention is especially useful in the production of compounds of the formula:

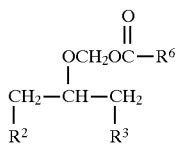

wherein $R^2$ and $R^3$ are both either chlorine or bromine, and $R^6$ is a $C_1$–$C_6$ alkyl group.

The formaldehyde donor which reacts with the alcohol, optionally in the presence of a catalyst, is a polyoxymethylene of the formula:

$$(CH_2O)_x \quad (III)$$

wherein x is between 1 and 5. In the second step of the process, the reaction product of alcohol and formaldehyde is reacted with a carboxylic acid anhydride. The carboxylic acid anhydride typically contains between 2 to 8 carbon atoms and is preferably derived from a $C_1$–$C_6$ aliphatic monocarboxylic acid.

The general reaction scheme of the invention may be represented as follows:

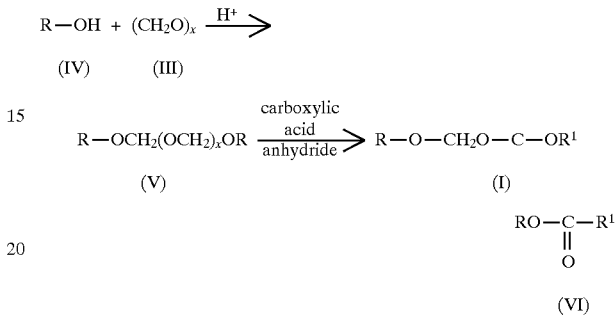

wherein R, $R^1$ and x are as designated above, $R^1$ being the organic moiety from the carboxylic acid anhydride.

Acetal oligomers of the formula V wherein x is 2–5 render a 2:1 ratio of compounds I:VI, respectively.

The resulting compounds are valuable intermediates in organic synthesis, especially for the preparation of 9-(1,3-dihydroxy-2-propoxymethyl)guanine.

In a particularly preferred embodiment, the invention relates to the production of the compound (I)

$$R\text{—}O\text{—}CH_2O\text{—}C\text{—}OR^1 \quad (I)$$

wherein R is a 1,3-disubstituted isopropyl radical. In a particularly preferred embodiment, the invention relates to the production of compounds of the formula:

wherein $R^2$ and $R^3$ are either halogen or $R^5$; $R^5$ is:

$$-O-C-R^6$$
$$\parallel$$
$$O$$

and further wherein $R^6$ is a $C_1$–$C_6$ alkyl group, preferably a $C_1$–$C_3$ allyl group, most preferably —$C_2H_5$.

Another embodiment of the invention is drawn to the novel intermediate represented by the formula (II) wherein $R^2$ and $R^3$ are halogen (—Cl and —Br preferred).

Encompassed within a preferred embodiment is the reaction of 1,3-dihalo-2-propanol (Formula IV wherein R is 1,3-dihaloisopropyl) with a formaldehyde donor (III) to render 1,3-dihalo-2-(propionyloxymethoxy)propane, represented by the formula (VII):

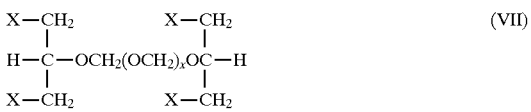

wherein X is Cl or Br. In the most preferred embodiment X is chlorine. Compound (VII) is then reacted with either propionic acid or acetic acid anhydride to form 1,3-dihalo-2-(propionyloxymethoxy)propane (VIII) or 1,3-dihalo-2-(acetyloxymethoxy)propane (IX), respectively:

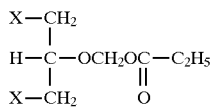

and

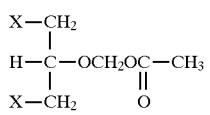

The compound of either formula (VIII) or (IX) may then be reacted with guanine to form the $N^2$,9-diacetylguanine (X) in accordance with the reaction scheme:

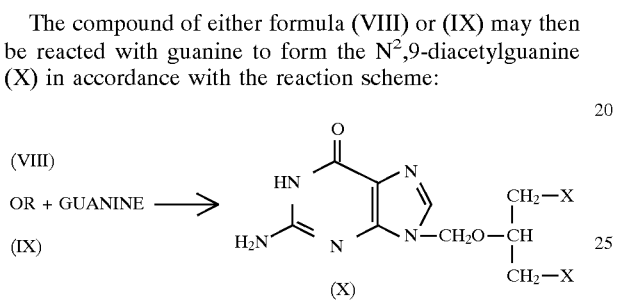

Also within the preferred embodiment of the invention is the reaction of a 1,3-diester derivative of isopropyl alcohol of formula (XI) with a formaldehyde donor, as represented by the reaction scheme:

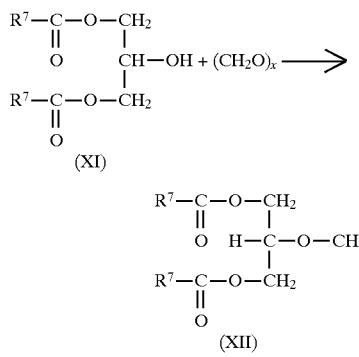

wherein $R^7$ is most desirably a $C_1$–$C_3$ alkyl group.

Compound XII is then reacted with a carboxylic acid anhydride derived from a $C_1$–$C_6$ monocarboxylic acid (preferably acetic acid anhydride or propionic acid anhydride), to render the compound of formula:

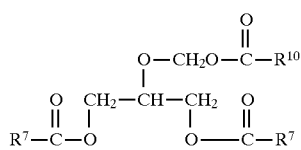

wherein $R^{10}$ is the organic moiety of the carboxylic acid anhydride. In a most preferred embodiment, compound XIV is produced:

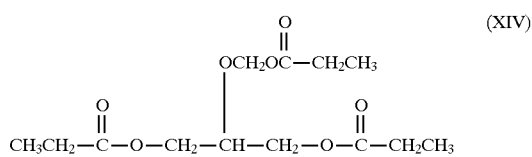

In another preferred embodiment the alcohol R—OH is of the formula:

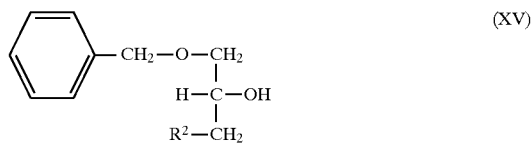

wherein $R^2$ is either chlorine or bromine.

The reaction of compound XV with formaldehyde donor proceeds as follows:

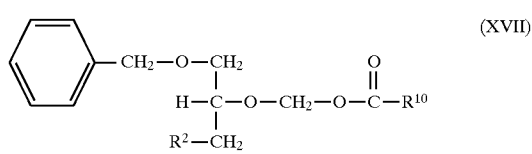

both of $R^2$ most preferably being —Cl. Compound XVI is then reacted with a carboxylic acid anhydride to render the intermediate product:

(XVII)

[structure: benzyl–$CH_2$–O–$CH_2$–CH(–$CH_2R^2$)–O–$CH_2$–O–C(=O)–$R^{10}$]

In a most preferred embodiment, $R^{10}$ is either —$CH_3$ or —$C_2H_5$.

The invention relates to a method for introducing an acyloxyalkoxy group, —$CH_2$—O—$COR^1$ directly onto an alcohol, without the use of a halogenated ester. Bischloroalkylethers therefore do not form.

The first phase of the process of the invention is the reaction of the alcohol R—OH (R being any of the groups set forth above) with a formaldehyde donor, preferably in the presence of a catalyst. The alcohol is of the formula R—OH wherein R is as designated above. Especially preferred as the alcohol are methanol, 1,3-dichloropropanol, 3-benzyloxy-1-chloro-2-propanol and the alcohol of formula XI.

The reactants are heated from about 22° C. to about 100° C., preferably 60° C., at pressures ranging from about 5 to about 760 mm Hg, preferably at atmospheric. The reaction is typically fairly rapid and generally is complete between 5 minutes to 12 hours. The reaction stops when all of the alcohol has been converted to the compound of formula (V). Reaction temperatures in excess of 60° C. are generally not preferred since they may result in the deposition of the formaldehyde donor in the reactor.

The preferred formaldehyde donor is paraformaldehyde though other forms are acceptable, such as trioxane, methylene dipropionate, methylene diacetate and formalin (37% water solution of formaldehyde).

The molar ratio of the alcohol:formaldehyde donor is generally 2:1 so as to favor the production of the alkoxylated product of formula V.

The catalyst may be concentrated or dilute acid such as sulfuric acid, paratoluenesulfonic acid, Amberlyst acidic sulfonic acid (such as Amberlyst 15 acidic resin), a Lewis acid, such as $FeCl_3$ or $AlCl_3$ or phosphoric acid. In addition to its catalytic effect, the catalyst operates in a dehydrating capacity. Where the R group of formula IV contains a substituted ether moiety, it may be desirable to consider the strength of the acid. Where R is substituted with an alkyl ether or benzyl ether group, it has been found most preferable to use a strong acid, such as sulfuric acid.

In a preferred reaction mode, the reaction mix, once heated to approximately 60° C. Nor about one hour, is cooled to between about 20° to about 40° C., preferably about 23°–270° C. A small exotherm has been noted when the reaction mix reaches 40° C. Though the formation of the acetal is an endothermic reaction, the heat of mixing of the acid and water often liberates enough energy to make the overall reaction slightly exothermic.

Compounds of formula (I) are then prepared by addition of a carboxylic acid anhydride to the compound of formula (V). Any carboxylic acid anhydride may be used, especially those derived from $C_1$–$C_6$ aliphatic carboxylic acids. In a preferred embodiment, acetic acid anhydride and propionic acid anhydride are used. The reaction is preferably conducted in the presence of an acid.

The reaction is conducted at a temperature between about 17° to about 60° C., preferably between 22° and 30° C. The reaction time is dependent on the feed rate.

The feed rate of acid anhydride to compound V occurs usually over 4 to 8 hours. Typically, water is consumed upon conversion of the anhydride to the free acid. The newly dehydrated system may then continue to convert any of the unreacted alcohol into the acetal oligomers. Conversions are readily appreciated from 65 to 85% under such conditions.

The carboxylic acid anhydride may be added directly to the reaction vessel which contains the product of formula (V). In such instances, it is most desirable not to add an excessive amount of carboxylic acid anhydride since side reactions with the desired product (I) will result. Generally, an equimolar ratio of the compound (V) and carboxylic acid anhydride is sufficient. Generally, the reaction is allowed to proceed until the concentration of product (V) drops below 0.1%. Typically, this may occur in less than 30 minutes. Ambient pressure is acceptable.

The reaction of alcohol and formaldehyde donor to form product (V) and water occurs at equilibrium. Thus, it is preferred to remove one or both of the products to drive the reaction forward. Normally, water is removed from the system. Water may be removed by use of anhydrous inorganic salts, vacuum stripping or by use of sulfuric acid. Vacuum stripping tends to decrease the amount of carboxylic acid anhydride needed in the process by removing the water of reaction from the system.

It is further desirable to add the carboxylic acid anhydride to the compound of formula (V) as soon as (V) is formed. This is attributed to the fact that the reaction of the formaldehyde donor and the alcohol occurs at equilibrium conditions. The slow addition of carboxylic acid anhydride shifts the equilibrium reaction of alcohol and formaldehyde donor to the formation of (V); thereby favoring the reaction of the carboxylic acid anhydride with the compound of formula (V). The process of the invention further removes residual formaldehyde by its reaction with the carboxylic acid anhydride.

Once product (I) has formed, the catalysts are quenched by the addition of a solid quenching agent, such as a carboxylic acid salt. The carboxylic acid anhydride will continue to react with compound (V) until the catalyst is neutralized. Water added to the system prior to the neutralization of the catalyst generally results in the regeneration of the compound of formula (V). In addition to affecting the product yield of (I), such reversal reactions interfere with the purity of the desired product.

Once the reaction is complete, the catalyst is neutralized. This can be accomplished with a base, preferably an alkali metal hydroxide or the carboxylic acid salt of an alkali metal, such as a sodium or potassium salt of a $C_1$–$C_5$ carboxylic acid. The quantity of base is about 1.1 molar equivalents based on the amount of acid catalyst.

Once substantially all of the catalyst has been removed, free carboxylic acid is removed by a caustic wash, such as 10% sodium hydroxide solution. The wash is performed at ambient temperature and atmospheric pressure. Typically the final temperature of the washed mixture is between about 55° to about 75° C.

The invention particularly relates to the production of the intermediates of the formula (II):

wherein $R^2$ and $R^3$ are either chlorine or bromine or $R^5$; $R^5$ is

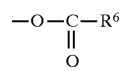

and further wherein $R^6$ is a $C_1$–$C_6$, preferably a $C_1$–$C_3$, alkyl group. In a preferred embodiment $R^2$ and $R^3$ are both either chlorine or bromine.

The production of compound (II) occurs in accordance with the following reaction sequence:

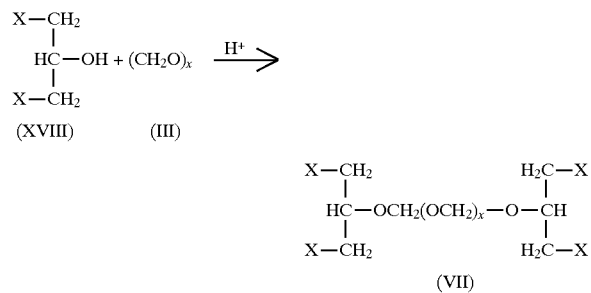

In this reaction, 1,3-dihalo-2-propanol XVIII (wherein X is preferably either chlorine or bromine) is reacted with formaldehyde donor III to produce the compound of formula (VII). Formula (VII) is then converted to the compound of formula (XIX):

by reaction of (VII) with a carboxylic acid anhydride, preferably with acetic acid anhydride or propionic acid anhydride.

Compounds of formula (II) may further be prepared by reacting 1,3-dihalopropanol with a formaldehyde donor and hydrogen halide to render the 2-halomethoxy-1,3-dihalopropane. This intermediate in turn is reacted with a carboxylic acid salt (such as sodium propionate).

Compounds of formula XVIII may further be prepared from the reaction product of formula XIX. This is done by adding either an alkali metal salt of acetic acid (wherein $R^7$ of formula XIII are both methyl) or propionic acid (wherein $R^7$ of formula XIII are both propyl) to the reaction product XIX. Typically the molar ratio of carboxylate salt: product XIX is between from about 2 to about 2.5. The reaction can be carried out in polar, aprotic solvents, such as dimethyl sulfoxide or dimethylformamide, or in an inert solvent, such as toluene, in the presence of a phase transfer catalyst, such as tetrabutylphosphonium chloride.

EXAMPLES

The following non-limiting examples bring out the more salient features of the invention.

Example 1

This example illustrates the synthesis of a compound of the formula:

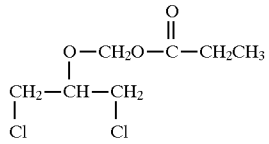

To a 5 liter round bottom flask was added 645 g (5.0 moles) of 1,3-dichloro-2-propanol. To the flask was also added about 165 g (5.49 moles) of paraformaldehyde and 40 g of concentrated $H_2SO_4$. The reaction mixture was stirred and gradually heated to a temperature of about 60° C. The reaction mixture was cooled to 25° C. as soon as the reaction temperature reached 60° C. Analysis of the crude mixture showed 21.91% acetal and 31.63% 1,3-dichloro-2-propanol. To the flask was then added 950 g (7.39 moles) of propionic acid anhydride over a four hour period. The reaction solution temperature was kept between 22° and 30° C. during the charging of the propionic acid anhydride. The reaction solution was stirred at ambient temperature for thirty minutes after the completion of the addition of the propionic acid anhydride.

About 85 g of sodium propionate was then added over ten minutes. The reactor temperature rose from 22° to 33° C. Next, a 10% NaOH solution (about 1500 g) was mixed with the crude solution over ten minutes, with the reactor temperature reaching 58° C. at the end of the base addition. The two phase system was agitated for 15 minutes, then allowed to phase for 30 minutes. The lower organic phase contained approximately 6.70% propionic acid, about 60.19% 1,3-dichloro-2-(propionyloxymethoxy)propane and 6.60% propionic acid anhydride. The reaction product contained no bis(chloromethyl)ether.

The product was then purified as follows. The aqueous upper phase was removed from the flask. The washed organic phase (1160.2 g, 48.95% of the product taken forward) was heated under vacuum conditions (pressure of about 6 mm Hg). The trap contents and light ends (16.4 and 328.3 g, respectively, 29.7% of charge weight) were removed over a period of 9.5 hours. The reflux ratio varied from 5:1 at the beginning of the strip to 20:1 at the end. The light end strip was determined to be complete when the content of 1,3-dichloro-2-(propionyloxymethoxy)propane in the overhead stream reached 52%. The light ends-stripped material (798.6 g) was taken forward to the product recovery step. The 1,3-dichloro-2-(propionyloxymethoxy)propane was then flash distilled at 8 mm Hg from 791.1 g of crude (propionyloxymethoxy)propane. The overhead temperature ranged from 116°–27° C. The pot temperature for the distillation was from about 122° to about 127° C. The product obtained, weighing about 747.2 g, consisted of 91.22 weight % 1,3-dichloro-2-(propionyloxymethoxy) propane. Of the GC-elutable portion of the bottoms, 91% was 1,3-dichloro-2-(propionyloxymethoxy)propane.

Example 2

This example illustrates the synthesis of a compound of the formula:

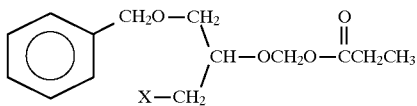

In a 12 liter flask 3-benzyloxy-1-chloro-2-propanol (5000 g, 24.9 moles) and paraformaldehyde (831 g, 27.7 moles) were added together. Then, sulfuric acid was added. The reaction mix was heated to 59°–61° C. Nor 1 hour. Upon cooling to 21° C. propionic anhydride (5291 g, 40.7 moles) was fed over 6 hours. The reaction temperature range was 18°–23° C. After the completion of the anhydride feed sodium propionate (428 g) was added to neutralize the catalyst.

The crude reaction mix was washed with 10% NaOH. The washed crude was distilled under vacuum (approximately 4 mm Hg). Thus was recovered 1-benzyloxy-3-propionyloxy-2-(propionyloxymethoxy) propane in 50.9% yield (94.0% purity).

Example 3

To a 12 liter round bottom flask was added 4,192 grams of dimethyl formamide, 454.5 grams (2.56 moles) of 2-chloromethoxy-1,3-dichloropropane and 985.9 grams (10.26 moles) of sodium propionate. The reaction mixture was heated with stirring to 72° C. over a one hour period. The reaction solution was cooled to 40° C. and the sodium chloride was filtered from the 1,3-dichloro-2-(propionyloxymethoxy)propane/dimethyl formamide mixture and was washed with 305.6 grams of dimethyl formamide. Analysis of the filtrate showed 12.7% 1,3-dichloro-2-(propionyloxymethoxy)propane (456 grams/2.12 moles).

The product was purified as follows. The dimethyl formamide was stripped from the filtered solution under vacuum conditions (pressure of about 20 mm Hg) with a reflux ratio of 1:2. The stripping was stopped when the kettle temperature reached 100° C. at 20 mm Hg. The kettle bottoms from the strip weighed 601.2 grams and was analyzed. It contained 73.07% 1,3 dichloro-2-(propionyloxymethoxy) propane (439.3 grams/2.04 moles).

The residue from the dimethyl formamide strip was charged to a one liter kettle attached to a 1" ID×24" vacuum jacketed column packed with 0.16 inch Pro-Pak stainless extruded column packing. The 1,3-dichloro-2-(propionyloxymethoxy)propane was distilled overhead under vacuum conditions (less than 1 mm Hg) at a reflux ratio of 4:1 for the first half and 3:1 for the remainder. The overhead temperature ranged from 25° C. to 50° C. and the kettle temperature ranged from 75° C. to 154° C. The distillation was terminated when the kettle was almost dry.

The product obtained, weighing about 338.7 grams, consisted of about 92.5% 1,3-dichloro-2-(propionyloxymethoxy)propane.

Having described the invention above, various modifications of the techniques, procedures, material and equipment will be apparent to those in the art. It is intended that all such variations within the scope and spirit of the appended claims be embraced thereby.

What is claimed is:

1. A process of preparing a compound of the formula

R—O—CH$_2$O—COR$^1$  (I)

wherein R is a C$_1$–C$_6$ alkyl, a C$_3$–C$_8$ cycloalkyl, an aryl or a benzyl group, the R group being optionally substituted with one or more phenoxy groups, benzyloxy groups, halogen atoms, a group of the formula:

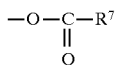

and —R$^8$—O—R$^9$; wherein R$^7$ and R$^9$ independently are a C$_1$–C$_6$ alkyl or haloalkyl group; R$^8$ is of the formula —(CH$_2$)$_y$, wherein y is 0 to about 6; and R$^1$ is a C$_1$–C$_6$ alkyl, R$^1$ being an organic moiety from a carboxylic acid anhydride, said process comprising reacting a polyoxymethylene of the formula:

R—O—CH$_2$(OCH$_2$)$_x$OR  (V)

wherein x is between 1 and 5 with a carboxylic acid anhydride containing about 2 to about 8 carbon atoms for a time and at a temperature sufficient to generate the compound of formula (I).

2. The process of claim 1 wherein the polyoxymethylene of formula (V) is prepared by reacting an alcohol of the formula R—OH with a formaldehyde donor.

3. The process of claim 2 wherein the formaldehyde donor is selected from the group consisting of formaldehyde, paraformaldehyde, trioxane, formalin and methylene diacetate.

4. The process of claim 2 wherein the reaction of alcohol and formaldehyde donor is conducted in the presence of a catalyst selected from the group consisting of paratoluenesulfonic acid, sulfonic acid, a Lewis acid, and phosphoric acid.

5. The process of claim 4 wherein the Lewis acid is selected from the group consisting of AlCl$_3$ and FeCl$_3$.

6. The process of claim 1 wherein the polyoxymethylene is of the formula:

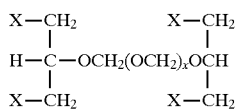

wherein X is halogen.

7. The process of claim 6 wherein X is independently selected from chlorine and bromine.

8. The process of claim 6 wherein the carboxylic acid anhydride is selected from the group consisting of acetic acid anhydride and propionic acid anhydride.

9. The process of claim 8 wherein x is 1.

10. The process of claim 1 wherein the polyoxymethylene is of the formula:

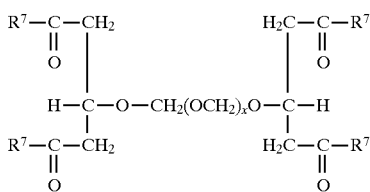

11. The process of claim 10 wherein each R$^7$ is —C$_2$H$_5$.

12. The process of preparing a compound of the formula:

R—O—CH$_2$O—COR$^1$  (I)

wherein R is a C$_1$–C$_6$ alkyl, a C$_3$–C$_8$ cycloalkyl, an aryl or a benzyl group, the R group being optionally substituted with one or more phenoxy groups, benzyloxy groups, halogen atoms, a group of the formula:

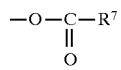

and —R$^8$—O—R$^9$ wherein R$^7$ and R$^9$ independently are a C$_1$–C$_6$ alkyl or haloalkyl group; R$^8$ is a —(CH$_2$)$_y$ group wherein y is between 0 to about 6; and R$^1$ is a C$_1$–C$_6$ alkyl group; said process comprising:

(a) reacting an alcohol of the formula R—OH and a formaldehyde donor in the presence of a catalyst for a time and at a temperature sufficient to generate a compound of the formula:

R—O—CH$_2$(OCH$_2$)$_x$OR  (V)

wherein x is between 1 and 5;

(b) reacting the product of (V) with a carboxylic acid anhydride having between about 2 to about 8 carbon atoms for a time and at a temperature sufficient to generate the compound of formula (I).

13. A process of producing a compound containing an acyloxyalkoxy group from an alcohol which comprises:

(a) reacting the alcohol of the formula R—OH wherein R is an organic moiety with a formaldehyde donor in the presence of a catalyst for a time and at a temperature sufficient to generate a compound of the formula:

R—O—CH$_2$(OCH$_2$)$_x$OR  (V)

wherein x is between about 1 to about 5; and (b) reacting the compound of formula (V) with a carboxylic acid anhydride of the formula (R$^1$CO)$_2$O wherein R$^1$ is a C$_1$–C$_6$ alkyl group for a time and at a temperature sufficient to generate a compound of the formula:

R—O—CH$_2$O—COR$^1$.

14. The process of claim 13 wherein the formaldehyde donor is selected from the group consisting of formaldehyde, paraformaldehyde, trioxane, formalin and methylene diacetate.

15. The process of claim 13 wherein the catalyst is a Lewis acid selected from the group consisting of AlCl$_3$ and FeCl$_3$.

16. The process of claim 13 wherein R$^1$ is a C$_1$–C$_3$ alkyl group.

17. The process of claim 13 wherein x is 1.

18. The process of claim 1 wherein the compound of the formula (I) is:

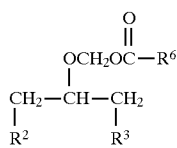

wherein $R^2$ and $R^3$ are both either chlorine or bromine, and $R^5$ is a $C_1$–$C_6$ alkyl group.

19. The process of claim 2 wherein the molar ratio of alcohol:formaldehyde donor is about 2:1.

20. The process of claim 12 wherein the alcohol and formaldehyde donor are reacted at a temperature of from about 22° C. to about 100° C.

21. The process of claim 20 where in the alcohol and formaldehyde donor are reacted at a temperature of from about 22° C. to about 60° C.

22. The process of claim 20 wherein the product (V) is reacted with the carboxylic acid anhydride at a temperature of from about 17° C. to about 60° C.

23. The process of claim 1 wherein the polyoxymethylene and carboxylic acid anhydride are in an equimolar ratio.

24. The process of claim 12 wherein the polyoxymethylene and carboxylic acid anhydride are in an equimolar ratio.

* * * * *

UNITED STATES PATENT AND TRADEMARK OFFICE
CERTIFICATE OF CORRECTION

PATENT NO. : 5,852,208
DATED : December 22, 1998
INVENTOR(S) : Joseph C. Rongione It is certified that error appears in the above-identified patent and that said Letters Patent is hereby corrected as shown below:

Column 13, line 10, "$R^5$" should read -- $R^6$ --.

Signed and Sealed this

Thirtieth Day of March, 1999

Attest:

Q. TODD DICKINSON

*Attesting Officer*   Acting Commissioner of Patents and Trademarks